United States Patent
Becker et al.

(10) Patent No.: US 9,636,307 B2
(45) Date of Patent: May 2, 2017

(54) ORAL PHARMACEUTICAL COMPOSITION COMPRISING TASTE-MASKED N-ACETYLCYSTEINE

(71) Applicant: HERMES ARZNEIMITTEL GMBH, Pullach (DE)

(72) Inventors: Karin Becker, Grobenzell (DE); Detlev Haack, Pullach (DE); Sharareh Salar Behzadi, Vienna (AT); Andreas Zimmer, Graz (AT)

(73) Assignee: HERMES ARZNEIMITTEL GMBH, Pullach (DE)

( * ) Notice: Subject to any disclaimer, the term of this patent is extended or adjusted under 35 U.S.C. 154(b) by 0 days.

(21) Appl. No.: 14/783,794

(22) PCT Filed: Apr. 11, 2014

(86) PCT No.: PCT/EP2014/057442
§ 371 (c)(1),
(2) Date: Oct. 9, 2015

(87) PCT Pub. No.: WO2014/167124
PCT Pub. Date: Oct. 16, 2014

(65) Prior Publication Data
US 2016/0067189 A1    Mar. 10, 2016

(30) Foreign Application Priority Data
Apr. 12, 2013   (EP) .................... 13163638

(51) Int. Cl.
*A61K 9/50*    (2006.01)
*A61K 9/51*    (2006.01)
*A61K 31/198*  (2006.01)

(52) U.S. Cl.
CPC .............. *A61K 9/5015* (2013.01); *A61K 9/50* (2013.01); *A61K 9/5089* (2013.01); *A61K 9/51* (2013.01); *A61K 9/5123* (2013.01); *A61K 31/198* (2013.01)

(58) Field of Classification Search
CPC ........... A61K 9/50; A61K 9/51; A61K 31/198
See application file for complete search history.

(56) References Cited

U.S. PATENT DOCUMENTS

| | | |
|---|---|---|
| 5,891,476 A | 4/1999 | Reo et al. |
| 2003/0180352 A1* | 9/2003 | Patel .................... A61K 9/1617 424/465 |
| 2006/0034937 A1* | 2/2006 | Patel .................... A61K 9/5078 424/497 |
| 2010/0068290 A1 | 3/2010 | Ziegler et al. |
| 2010/0092569 A1 | 4/2010 | Lorenzon |

FOREIGN PATENT DOCUMENTS

| | | |
|---|---|---|
| EP | 0 839 528 A1 | 5/1998 |
| WO | WO2008071407 A2 | 6/2008 |
| WO | WO2010070028 A1 | 6/2010 |

OTHER PUBLICATIONS

Griffin, Calculation of HLB Values of Non-Ionic Surfactants, Journal of the Society of Cosmetic Chemists, 5 (4): 249-256, 1954.
International Search Report of Corresponding International Application PCT/EP2014/057442, May 22, 2014.

* cited by examiner

*Primary Examiner* — Carlos Azpuru
(74) *Attorney, Agent, or Firm* — Hoxie & Associates LLC

(57) ABSTRACT

The invention provides coated particles with taste-masked N-acetylcysteine. The particles comprise a core with the active ingredient and a coating comprising a triglyceride and a surfactant. The particles exhibit rapid drug release and a stable release profile. Moreover, the invention provides a hot-melt coating method for manufacturing such particles, and pharmaceutical compositions comprising the particles. The method allows the coating of core particles at moderate temperatures, thereby preventing the degradation of the thermolabile active ingredient.

11 Claims, No Drawings

ORAL PHARMACEUTICAL COMPOSITION COMPRISING TASTE-MASKED N-ACETYLCYSTEINE

CROSS REFERENCE TO RELATED APPLICATIONS

This application is a United States Application under 35 U.S.C. §371 claiming benefit of PCT Application No. PCT/EP2014/057442, filed on Apr. 11, 2014, which claims the benefit of European Patent Application No. 13163638.3, filed on Apr. 12, 2013, the contents of each of which are incorporated herein by reference in their entireties.

FIELD OF THE INVENTION

The present invention relates to the field of pharmaceutics, and concerns oral drug formulations, their manufacture and their use.

BACKGROUND OF THE INVENTION

Most patients prefer to take orally administered medicaments over other routes of administration. However, in order to be acceptable to patients, an oral drug product must be easily swallowed and without unpleasant or bitter taste or other undesirable organoleptic properties.

N-acetylcysteine, or N-acetyl-L-cysteine, often also abbreviated as NAC, is a mucolytic agent used in many countries in the management of symptoms associated with cough and the common cold. Other uses include the treatment of paracetamol overdose and sulphate depletion. The compound has a highly unpleasant taste and develops a smell of sulphur, especially over time through trace degradation.

As a mucolytic agent, N-acetylcysteine is typically administered at a dose of 200 mg three times a day, or more commonly 600 mg once a day. Because such dose can only be accommodated in relatively large dosage units which may not be easy to swallow, the compound is often formulated as an effervescent tablet or effervescent granules which are much easier to take than a conventional tablet or capsule containing such high dose.

While taste masking is generally rather easy to achieve with a conventional tablet which may be coated with a suitable polymeric coating, and also in the case of a capsule formulation wherein the capsule shell itself provides a barrier which prevents contact between the active ingredient and the oral mucosa of the patient during administration, it is more challenging to mask the taste of a compound like N-acetylcysteine when formulated as a dispersible, effervescent, or orally disintegrating dosage form or as granules for direct oral administration ("direct-to-mouth granules"), because in these cases the dosage unit is not swallowed as a whole, but the formulation comes into substantial contact with the oral mucosa. In the case of effervescent formulations, the drug typically dissolves in a larger amount of water, such as 200 mL, and in this diluted form, sufficient taste masking may be achieved through the incorporation of sweetening agents and flavours. Most challenging in terms of taste is the formulation of the active ingredient in dosage forms whose administration potentially allows the drug to contact the oral mucosa in concentrated form, as in the case of orally disintegrating tablets or granules for direct oral administration. On the other hand, such dosage form designs are highly desirable for high-dose drugs because of their excellent swallowability even without water.

Some compositions comprising N-acetylcysteine and taste-masking components are known. For example, EP-A 0 839 528 discloses N-acetylcysteine tablet or granulate compositions formulated with cyclodextrins, which are complexing agents with cavities capable of hosting small molecules. In addition, the formulations comprise sweetening agents such as sorbitol and aspartame, and various flavours. However, cyclodextrins are expensive excipients, and for effective taste-masking require incorporation in relatively large amounts. Also the use of sweeteners and flavouring agents to divert the patient from an active ingredient's unpleasant sensory attributes often requires the use of large amounts of these excipients to achieve a good taste-masking effect. According to EP-A 0 839 528, the active ingredient is incorporated into the formulations only at a level of 5 to 10 wt.-%.

A generally more effective taste-masking approach is to provide a coating on the surface of the active ingredient. The coating serves as a physical barrier layer between the active ingredient and the patient's taste buds and olfactory receptors.

In addition, a coating may be useful also to protect a sensitive or labile active ingredient during storage.

In principle, taste-masking coating may be polymeric film coatings or lipidic coatings. Polymeric coating systems are sprayed onto drug cores as aqueous or organic solutions or dispersions. A disadvantage of organic solvents is their need for special equipment and their negative impact on the environment. Aqueous coating systems also consume substantial energy, as the polymeric coating material must be heated above its film-forming temperature in order to coalesce, and the removal of water require more extensive drying than that of typical organic solvents. Moreover, many polymeric coating systems show curing effects, i.e. their properties change over time, so that the drug dissolution behaviour may become compromised during storage.

Lipidic coating systems, such as coatings based on waxes like carnauba wax, do not require a solvent to be applied to drug-containing cores: They may often be used as melts in hot-melt coating processes. On the other hand, these types of coatings, due to the poor water solubility of its main constituents, also tend to have substantial negative impact on the drug's release profile, especially if rapid drug release is required. In such cases, wax coatings are often not successful.

Moreover, the stability of a lipidic or waxy taste-masking coating itself over time can also impact the release profile of the active ingredient. The conversion of an initially formed polymorph of a coating excipient to a thermodynamically more stable crystal form over time during the course of storage, sometimes also triggered by an exposure to different environmental conditions, can lead to significant and undesirable variations in the drug dissolution profile of the composition.

Furthermore, also the hot-melt processing conditions may be critical to temperature-sensitive drug compounds like N-acetylcysteine. Depending on the type of lipidic or waxy coating material, the coating process are sometimes conducted at temperatures of higher than 60° C., and sometimes also higher than 80° C. or even 100° C.

For these reasons, no suitable method for providing N-acetylcysteine with a taste-masking coating has been developed so far, even though there is a clear need for such coated N-acetylcysteine.

WO 2008/071407 A2 discloses immediate or rapid release pellets comprising cefpodoxim, an antibiotic compound having a poor taste. The pellets exhibit a taste-masking coating comprising carnauba wax and a hydrogel former such as a cellulose polymer derivative, alginate or gum. It is mentioned in the document that many lipophilic substances, such as cocoa butter or Precirol, are prone to polymorphic changes during storage. As the structural changes would lead to inconsistencies in the dissolution profiles, such compounds are deemed to be unsuitable for use as coating excipients for these pellets. The document therefore teaches the use of waxes such as carnauba wax which have a high melting range and which do not exhibit any polymorphic changes.

U.S. Pat. No. 5,891,476 discloses acetaminophen particles or granules coated with a non-polymorphic waxy component such as carnauba wax and optionally other lipid components and/or surfactants. According to the document, the use of such waxes removes the risk of variable dissolution rates resulting from changing morphology of the coating over time and under different conditions.

However, a disadvantage in using waxy components having a high melting point such as carnauba wax (melting range approx. 82 to 86° C.) in hot-melt coatings is that the active ingredient itself may also be subjected to the higher temperatures required to maintain the coating components in melt-phase during the coating process. Higher temperatures during processing can increase the degradation of thermolabile active ingredients. Moreover, hot-melt coating processes involving molten carnauba wax are very difficult to handle because the coating composition must be kept at even higher temperatures, e.g. at about 100° C. or higher, and since this wax solidifies very rapidly upon cooling down, it tends to clog the tubes through which it is pumped to the spray nozzle, as well as the nozzle itself.

WO 2010/070028 A1 discloses various taste-masked, hot-melt coated compositions incorporating the active ingredients acetaminophen, ranitidine, and caffeine. The coatings comprise, as a meltable lipophilic excipient, stearic acid, Precirol ATO 5 (a mixture of mono-, di- and triglycerides of palmitic and stearic acid), or Compritol 888 ATO (glyceryl behenate). The coatings further comprise a release compound, i.e. a compound which enhances the disintegration of the taste-masking layer in the gastrointestinal fluid, such as by the formation of pores or holes through swelling (e.g. Amberlite IRP 88) or carbon dioxide release (e.g. calcium carbonate); and a surfactant or other substance (e.g. PEG 3000 or Tween 20) which is incorporated to achieve a homogeneous distribution of the release compound in the meltable lipophilic excipient. However, the resulting coating compositions are rather complex. Due to the insolubility of the release compound in the meltable lipophilic compound, there is a risk of phase separation during the coating process, leading to poor reproducibility. Moreover, as the document is silent on this aspect, it is unclear whether the release profiles achieved with such complex and inherently incompatible coating compositions are stable under storage conditions.

US 2010/0092569 A1 relates to the taste-masking of conjugated linoleic acid compounds by suspending an adsorbate of the active ingredient on silica powder in a molten lipid matrix and subsequent spray cooling, such as to form coated particles. The lipid matrix comprises triglycerides of C16, C18, C20 and C22 saturated fatty acids and 3 wt.-% of an unidentified emulsifier whose function is to ensure a homogeneous dispersion of the active ingredient in the molten lipid. The purpose of the coating is to protect the light- and air-sensitive linoleic acid compound from degradation. The taste-masked product is used as an additive in animal feed.

However, the preparation of a melt suspension involves the full exposure of the active ingredient to temperatures higher than the melting range of the lipid, in the present case about 70° C., which may be acceptable in the case of some active ingredients or in the case of animal feeds, but not for temperature-sensitive pharmaceutical compounds for human use. Moreover, the document is silent as to the resulting dissolution profiles, which do not appear to have any relevance in this case.

It is an object of the invention to provide an improved method for the taste-masking of N-acetylcysteine. Moreover, it is an object to provide an improved taste-masked form of N-acetylcysteine which exhibits rapid drug dissolution and a stable dissolution profile. A further object is to provide improved pharmaceutical compositions comprising taste-masked N-acetylcysteine with rapid drug dissolution. A yet further object is to provide taste-masked compositions which may be manufactured at moderate temperatures in order to avoid the degradation of sensitive compounds such as N-acetylcysteine, as well as processes by which taste-masked compositions of sensitive compounds may be prepared. Moreover, it is an object to overcome one or more of the limitations or disadvantages associated with the prior art. Other objects will become clear on the basis of the description and the claims.

These and other objects are achieved by the subject-matter as defined in the independent claims below, with particular embodiments outlined in the dependent claims.

SUMMARY OF THE INVENTION

The invention provides, according to a first aspect, a coated particle which comprises a core and a coating. The core comprises the active ingredient, N-acetylcysteine, and the coating comprises a triglyceride which is solid at room temperature and a surfactant.

The core may consist of particles of the active ingredient, or it may be an agglomerated particle, such as a granule or pellet, comprising the active ingredient and one or more pharmaceutical excipients.

The solid triglyceride is preferably a saturated triglyceride. Its three fatty acid chains may be identical, as in trimyristin (or glyceryl trimyristate), tripalmitin (or glyceryl tripalmitate), tristearin (or glyceryl tristearate), triarachidin (or glyceryl triarachidate), or tribehenin (or glyceryl tribehenate) Tripalmitin and tristearin are among the preferred triglycerides.

The surfactant may be a non-ionic surfactant, such as a polysorbate. Polysorbate 65 is one of the preferred surfactants, in particular in combination with a saturated triglyceride selected from tripalmitin and tristearin. Optionally, the weight ratio of the triglyceride to the surfactant may be in the range from 70:30 to 90:10, in particular in the case of tripalmitin or tristearin and polysorbate 65. The coating may essentially consist of the triglyceride and the polysorbate.

In a further aspect, the invention provides a method for the preparation of coated particles comprising a core with N-acetylcysteine and a coating with a triglyceride which is solid at room temperature and a surfactant. The method includes the steps of (a) providing a core particle comprising N-acetylcysteine, (b) providing a coating composition comprising a molten triglyceride and a surfactant, and (c) coating the core particle with the coating composition. It is preferably carried out in a fluid-bed coater or in an air flow bed coater. The product temperature may be kept at about 20 to 50° C. during the coating step (c).

In yet a further aspect, the invention provides a pharmaceutical composition comprising coated particles comprising a core with N-acetylcysteine and a coating with a triglyceride which is solid at room temperature and a surfactant. The composition may optionally be formulated as granules, such as dispersible granules, effervescent granules, direct-to-mouth granules, or as a tablet, such as a dispersible tablet, an effervescent tablet, or an orally disintegrating tablet.

DETAILED DESCRIPTION OF THE INVENTION

In a first aspect, the invention provides a coated particle which comprises a core and a coating. The core comprises N-acetylcysteine, and the coating comprises a triglyceride which is solid at room temperature and a surfactant.

In the pharmaceutical field, a particle may generally refer to a primary particle, such as a crystal, or an agglomerated particle, such as a granule or pellet. According to the invention, the particle has a specific structure, comprising at least one core and at least one coating layer. The particle is useful as a component of a pharmaceutical composition for oral use.

The core is typically solid, optionally semi-solid, and comprises a pharmacologically active ingredient, N-acetylcysteine. The core itself also represents a primary or secondary particle, i.e. a crystal, a non-crystalline or partially crystalline particle, an agglomerated particle, a pellet, a micropellet, a granule, or a microparticle. The shape of the core primarily depends on the nature, composition and manufacturing method of the core material.

The particle size of the core as determined by sieving is typically below about 3 mm, and preferably below about 2 mm. In further preferred embodiments, the particle size of the core is from about 50 to about 1,000 μm, from about 80 to about 600 μm, from about 100 to about 400 μm, or from about 300 to 800 μm, respectively. In some other preferred embodiments, the particle size of the core is from about 250 to 550 μm, or from about 250 to 750 μm.

Optionally, the core substantially consists of N-acetylcysteine. In this context, the term "substantially consists of" means that no further components have been added to the active ingredient in order to prepare the core. Nevertheless, very small amounts of other materials may be present, such as impurities.

Alternatively, the core may be a composite particle, or a formulated particle, comprising N-acetylcysteine and at least one pharmaceutically acceptable excipient. For example, a granule, pellet or micropellet comprising N-acetylcysteine and at least one binder may be used. Commonly known methods for formulating and manufacturing such granule, pellet or micropellet may be used.

The coating is understood as a layer, or several layers, of material substantially enclosing the core, or at least the majority of the core surface. As it is an important objective of the invention to provide effective taste-masking of the active ingredient, it is preferred that at least 80% of the surface, or at least 90% of the surface, or at least 95% of the surface, or substantially all of the surface of the core is covered by the coating. At the same time, it will be appreciated by a person skilled in pharmaceutics that a bulk material comprising multiple particles according to the invention may include a minor fraction of particles whose coatings may not completely or substantially cover the cores, even though the majority of the particles exhibit substantially complete coatings.

The composition of the coating is of key importance to the invention. It comprises at least a triglyceride which is solid at room temperature and a surfactant. As used herein, a triglyceride is an ester derived from glycerol and three fatty acids. A triglyceride may also be referred to as a triacylglyceride, or a fat.

Solid at room temperature means that the lower limit of the melting range of the triglyceride is higher than about 20° C. More preferably, the lower limit of the melting range of the triglyceride is higher than about 35° C. In other preferred embodiments, the melting range is from about 40° C. to about 85° C., or from about 45° C. to about 70° C. If more than one triglyceride is present in the coating, at least one of them representing a large fraction of the total triglyceride content in the coating should have a melting range according to one of these preferences. It is understood that the melting ranges are—as usually—given for a normal atmospheric pressure, e.g. approximately 1013 mbar.

In particular native triglycerides often comprise fatty acid residues with different chain lengths and degrees of saturation, i.e. they represent mixtures of various chemically different triglycerides. For the sake of achieving more reproducible properties, triglycerides are therefore sometimes purified or semi-synthetically manufactured. Such more defined grades of triglycerides are also preferred according to the invention.

According to one of the preferred options, the triglyceride is a substantially pure triglyceride, having a chemical purity of at least about 90%, i.e. comprising only a small fraction of triglycerides with other fatty acid residues than the main fraction. In particular, the chemical purity of the triglyceride may be at least about 95%, or at least about 97%, respectively.

According to another one of the preferred options, the triglyceride is substantially saturated. In particular, the iodine value, which is a commonly used parameter to describe the degree of unsaturation in triglycerides and which reflects the mass of iodine in grams that is consumed by 100 grams of a triglyceride, may be lower than about 10, or not higher than about 5, or not higher than about 2, or not higher than about 1, respectively.

According to a further preferred option, the fatty acid residues of the triglyceride are substantially the same, i.e. at least about 80%, or at least about 90%, or even at least about 95% of the acyl chains have the same number of carbon atoms and degree of saturation. Particularly useful are saturated triglycerides having acyl residues of 10 to 30 carbon atoms. Especially preferred are saturated triglycerides having acyl residues with a chain length of 14 to 22 carbon atoms. Moreover, the triglyceride may be selected from trimyristin (mp ca. 56-57° C.), tripalmitin (mp 61-65° C.), tristearin (mp ca. 70-73° C.), triarachidin (mp ca. 76-80° C.) and tribehenin (mp ca 82-86° C.) respectively, especially from tripalmitin and tristearin. Optionally, two or more of these triglycerides may be used in combination.

Tripalmitin and tristearin, like many other saturated triglycerides, exhibit polymorphism. These triglycerides have an amorphous form and various crystalline forms, i.e. an unstable α-modification, a metastable β'-modification and a thermodynamically stable β-modification. Tripalmitin (in its stable β-form) typically has a melting range—as determined by DSC—of 61 to 65° C., whereas the melting range of tristearin is about 70 to 73° C.

Apart from the triglyceride, the coating comprises a surfactant. It has been surprisingly found by the inventors that coating compositions comprising certain surfactants in combination with a solid triglyceride, in particular non-ionic surfactants such as polysorbates, may be applied as hot-melt coatings at relatively low temperatures while leading to coated particles which do not undergo any major changes with respect to their drug release behaviour. Thus, the invention allows the coating of temperature-sensitive drugs such as N-acetylcysteine while achieving a product with significantly improved physical stability.

This is in sharp contrast to the teachings of prior art according to which the use of triglycerides as hot-melt coating materials is discouraged because the polymorphism of the triglyceride leads to dissolution profiles changing over time. Without wishing to be bound by theory, the inventors currently believe that the surfactant content in the coating composition leads to an induction of the thermodynamically stable δ-modification of the triglyceride at moderate temperatures, i.e. substantially below the recrystallisation temperature of the triglyceride, so that the β-modification is already formed at the time when the coating composition, applied to the core as a hot-melt, solidifies while cooling down, or shortly thereafter, i.e. within minutes or a few hours at the most. Without the surfactant content, the stable β-modification of tristearin, for example, would only be obtained at a temperature close to 60° C., and such temperature would be detrimental to thermolabile compounds such as N-acetylcysteine.

In other cases, it may also be possible that the surfactant stabilises the α-form of the triglyceride. In both cases, the consequence is that no polymorph conversion takes place during storage, and thus no physical change to the coating with potential impact on the drug dissolution profile.

In one of the preferred embodiments, the coating comprises no further lipid or wax component other than the triglyceride described above. In particular, the coating may be free of higher melting components which require increased processing temperatures or which could lead to an obstruction of the spray nozzle, such as carnauba wax.

The surfactant in the coating is optionally a non-ionic surfactant. Examples of pharmaceutically acceptable non-ionic surfactants include, without limitation, polysorbates, mono- and diglycerides of fatty acids, propylene glycol esters, sucrose fatty acid esters, polyglycerol esters, sorbitan fatty acid esters, polyoxyethylene sorbitan fatty acid esters, polyoxyethylene fatty acid ethers and poloxamers. In particular, polysorbates, such as polysorbate 65, have been found very suitable in combination with tristearin and tripalmitin. Optionally, two or more surfactants may be used in combination.

The surfactant, in particular the non-ionic surfact, according to one of the preferred options, has a hydrophilic-lipophilic balance (HLB) value in the mid-range, in particular from about 5 to about 15, as described by Griffin (Calculation of HLB Values of Non-Ionic Surfactants, Journal of the Society of Cosmetic Chemists 5 (4): 249-56, 1954). Also preferred is a non-ionic surfact with an HLB value in the range from about 6 to about 14, or from about 7 to about 13, or from about 8 to about 12, respectively. For example, polysorbate 65 exhibits an HLB value of about 10.5, and polysorbate 85 has an HLB value of about 11.

Alternatively, the surfactant in the coating may also be an ionic surfactant, such as a phospholipid or sodium dodecyl sulfate. Optionally, two or more surfactants may be used in combination. Further optionally, two or more surfactants comprising at least one ionic surfactant and at least one non-ionic surfactant may be used in combination.

In order to achieve a pronounced stabilising effect on the triglyceride in the coating, it is recommended to incorporate the surfactant at a surfactant-to-triglyceride ratio of at least about 0.05. More preferably, the ratio is in the range from about 0.05 to about 0.5, such as about 0.1, 0.15, 0.2, 0.25, 0.3, 0.35, 0.4, or 0.45. The coating composition may comprise, or even essentially consist of, from about 50 to 95 wt.-% of triglyceride and from about 5 to 50 wt.-% surfactant, in particular from about 70 to 95 wt.-% of triglyceride and from about 5 to 30 wt.-% surfactant.

Preferably, the surfactant is dissolved in, or miscible with, the triglyceride in the molten state, i.e. the surfactant is not incorporated at level which results in the formation of an emulsion or suspension in the molten state in which the coating composition is applied to the core particle. In this way, there is little risk for the coating composition comprising the surfactant and triglyceride to separate into two phases at any time during or after the coating process, and e reduced risk for the clogging of nozzles during the coating process, as in the case of a suspension, The coating may be free of other constituents. In fact, one of the preferred coating compositions essentially consists of about 70 wt.-% of tristearate and about 30 wt.-% of polysorbate 65. Another preferred coating composition essentially consists of about 90 wt.-% of tripalmitin and about 10 wt.-% of polysorbate 65. Applying one of these coating compositions to N-acetylcysteine particles as a hot-melt is surprisingly effective in simultaneously achieving effective taste-masking as well as rapid drug release, without release profile changes during storage.

Alternatively, the coating may comprise one or more further excipients, such as one or more pore-forming agents, fillers, dyes or colouring agents, stabilisers, antioxidants, sweeteners, flavours, swelling agents, and the like.

Preferably, however, the triglyceride and the surfactant together represent at least about 50 wt.-% of the coating, and more preferably at least about 70 wt.-%, or at least about 80 wt.-%, 90 wt.-%, or 95 wt.-%, respectively. According to a further preferred option, any further excipients are only incorporated at a level in which they are dissolved in, or miscible with, the molten triglyceride when the coating composition is sprayed onto the core particle.

The thickness of the coating is selected with an eye on the size and shape of the core. For example, if core particles shaped as flakes or needles are to be taste-masked, this may require a larger relative amount of coating composition to be applied than in the case of substantially spherical core particles having the same surface area. It will be appreciated by the skilled person that different weight ratios of the coating to the core are required for different core sizes to obtain the same coating thickness.

For example, for the coating of typical, somewhat irregularly shaped N-acetylcysteine particles having a mass mean particle size, as determined by sieve analysis, in the range from about 250 to about 750 μm, the amount of coating composition required to achieve taste-masking is at least about 20 wt.-%, and more preferably at least about 30 wt.-%, relative to the weight of the coated particles. For a more effective taste-masking, it may even be required to apply about 40 wt.-% of the coating composition or more, or about 50 wt. % or more. On the other hand, the relative amount of coating composition should not be so high as to result in slow drug dissolution from the coated particles. In the present example, the amount should therefore not be higher than about 75 wt.-%, such as about 70 wt.-% or less, or about 60 wt.-% or less, relative to the weight of the coated particles. Depending on the coating composition and the size and shape of the core particles, particularly useful ranges for the relative amount of coating compositions may be from about 20 to 70 wt.-%, or from about 30 to 50 wt.-%, or from about 40 to 60 wt.-%, or from about 50 to 70 wt.-%.

In one of the particularly useful embodiments which simultaneously achieves effective taste-masking, rapid drug release, and a stable dissolution profile, core particles of N-acetylcysteine having a mass mean particle size of about 250 to about 750 µm are coated with a coating essentially consisting of 70 wt.-% of tristearin and about 30 wt.-% of polysorbate 65, wherein the coating is applied as a hot-melt to the core particles at an amount of about 40 to 60 wt.-%, such as 50 wt.-%, relative to the weight of the coated particles. In another one of the particularly useful embodiments, the same core particles are coated with a coating essentially consisting of 90 wt.-% of tripalmitin and about 10 wt.-% of polysorbate 65, wherein the coating is applied as a hot-melt to the core particles at an amount of about 30 to 50 wt.-%, such as 40 wt.-%, relative to the weight of the coated particles.

The coated particle according to the invention may be manufactured by various methods, including the coating of core particles by conventional solvent-based coating methods in which the coating composition is dissolved in an organic solvent and subsequently sprayed onto the core particles under conditions by which the solvent is evaporated.

More preferably, however, the coating composition is melted and sprayed as a hot-melt onto the core particles. In this manner, the use of an organic solvent and the associated negative environmental, health and safety hazards may be avoided. One of the aspects of the invention is a method for the preparation of the coated particle described above, comprising the steps of (a) providing a core particle comprising N-acetylcysteine, (b) providing a coating composition comprising a molten triglyceride and a surfactant, and (c) coating the core particle with the coating composition.

The method may be carried out in any suitable coating equipment, whose precise configuration is selected in particular in consideration of the particle size of the core material. For example, the method may be performed in a fluid-bed coater or in an air flow bed coater.

One of the particular advantages of the invention is that the coating composition allows processing at rather low temperatures, thus being suitable for the processing of drug substances which are sensitive to degradation at elevated temperatures. N-acetylcysteine is an example of such sensitive active ingredient, for which reason it is not very suitable for being coated with hot-melt coating compositions requiring a high coating temperature, such as coating compositions based on carnauba wax or other waxes.

Preferably, the product temperature during the coating process is kept below about 60° C., in particular below about 55° C. According to a further preference, the product temperature is kept between about 20 and 50° C. while the coating composition is applied to the core particles as a melt. In this respect, the nature of the triglyceride in the coating should also be taken into account: In the case of a coating composition based on a lower melting triglyceride such as tripalmitin, the product temperature may be kept between about 20 and 35° C., whereas in the case of a coating composition based on a higher melting triglyceride such as tristearin, the product temperature may be kept between about 20 and 50° C., in particular between about 35 and 50° C., such as between about 40 and 48° C.

It has been found that the decomposition of N-acetylcysteine is notably suppressed at a temperature between about 40 and 48° C.—compared to working at above 50° C., as is already evident by the substantially reduced sulphurous smell during the processing of the material. Furthermore, stability testing of N-acetylcysteine revealed that no sulphur species are detectable by headspace gas chromatography from a sample of N-acetylcysteine treated at 40° C. for 2 hours. In contrast, two sulphurous species, acetyl mercaptane and s-ethyl ethanthioate, were detected from a sample of N-acetylcysteine subjected to 60° C. for 2 hours.

In a further aspect, the invention provides a pharmaceutical composition comprising the coated particle described above. While the drug N-acetylcysteine may also be administered by injection or inhalation, the coated particles as disclosed herein a particularly suitable for being incorporated in a composition for oral administration, in particular in the form of granules, such as dispersible granules, effervescent granules, direct-to-mouth granules, or as a tablet, such as a dispersible tablet, an effervescent tablet, or an orally disintegrating tablet.

Particularly useful embodiments are oral formulations which consist of multiple units, or which disintegrate in the mouth of the patient into multiple units, such as direct-to-mouth granules or orally disintegrating tablet, because for these types of formulations the taste-masking effect of the multiple units is crucial for patient acceptability.

As used herein, direct-to-mouth granules are oral compositions designed for direct oral administration without water. Direct-to-mouth granules may represent mixtures of various types of multiple units, which units may be agglomerated and/or non-agglomerated particles. Often, such direct-to-mouth compositions represent mixtures of sweetening agents, such as sugars or sugar alcohols, flavours, and drug, any of which may be agglomerated or granulated.

An orally disintegrating tablet may be defined as solid single-unit dosage forms that rapidly disintegrates in the mouth of the patient without chewing, typically within less than about one or two minutes. Orally disintegrating tablets are usually pressed with lower compression forces than conventional tablets to obtain a higher porosity. Alternatively, their porosity may be increased by a drying or sublimation step for those tablets which contain a high amount of moisture or a sublimable excipient. With regard to their formulation, the optimised use of disintegrants, such as commonly used crosslinked polymers, low-substituted celluloses, or effervescent couples, further contribute to rapid disintegration. Popular is also the use a highly water soluble excipients which allow the actual dissolution of major parts of the formulations in the saliva, and which give a smoother mouthfeel compared to other formulations that disintegrate rapidly but leave mostly insoluble residues behind.

Further embodiments, options, and/or preferences are illustrated by the following examples.

EXAMPLE 1

Hot-Melt Coating of N-Acetylcysteine with Tripalmitin and Polysorbate 65

300 g of N-acetylcysteine crystals (core particles) having a mean particle size of 550 µm and 0.3 g of Aerosil were fluidised in a laboratory scale air flow bed coater (Ventilus V-1, Innojet Herbert Huettlin, Steinen, Germany) and maintained at a temperature of 40° C. A molten mixture of 90 wt.-% of tripalmitin (Dynasan 116) and 10 wt.-% of polysorbate 65 (Tween 65) was stirred at a temperature of 100° C. The molten coating composition was then sprayed onto the N-acetylcysteine crystals at a spray rate of 5 g/min with an atomising pressure of 0.75 bar. It was confirmed by visual inspection that the core particles were not agglomerated but coated with the coating composition. The coated particles comprised about 50 wt.-% of coating material relative to their total weight.

Subsequently, the coated particles were tested with respect to their taste and dissolution behaviour. The dissolution test was carried in a paddle apparatus (USP). 1200 mg of the coated particles were placed in dissolution vessels filled with 900 mL of 0.1 N HCl and stirred at 100 rpm. The N-acetylcysteine content was analysed by an established HPLC method (according to Ph. Eur.). Taste-masking was evaluated by a panel of experts using a subjective organoleptic taste test. Water (1 mL) was injected into the oral cavity of a participant before intake of a sample. An amount of coated particles equivalent to a 600-mg dose of N-acetylcysteine was used for taste testing. The time prior to the participant's sensation of a sour or unpleasant taste was recorded.

In result, it was found that the coated particles released 96% of the active ingredient after 15 minutes. The taste was found to be acceptable, as no unpleasant or sour taste could be detected within 30 s, i.e. the coating provided effective taste masking.

Some of the product was placed in sachets or glass bottles and stored for 3 months at 25° C./60% r.h., 30° C./65% r.h. and 40° C./75% r.h., respectively, after which period the dissolution test was repeated. There was no significant difference in the dissolution profiles after 3 months of storage.

EXAMPLE 2

Hot-Melt Coating of N-Acetylcysteine with Tristearin and Polysorbate 65

The same procedures as in Example 1 were followed, except that the coating composition was a mixture of 70 wt.-% of tristearin (Dynasan 118) and 30 wt.-% of polysorbate 65 (Tween 65), the product temperature was kept at 40° C. during the coating process, and the relative amount of coating in the coated particles was 50 wt.-%.

In result, it was found that the coated particles released 83% of the active ingredient after 15 minutes. The taste was found to be acceptable, i.e. the coating provided effective taste masking.

Some of the product was placed in sachets and stored for 3 months at 25° C./60% r.h., 30° C./65% r.h. and 40° C./75% r.h., respectively, after which period the dissolution test was repeated. There was no pronounced difference in the dissolution profiles after 3 months of storage.

EXAMPLE 3

Taste-Masked Coated N-Acetylcysteine Particles

A similar procedure as in Example 1 was followed. The molten coating composition was sprayed onto the N-acetylcysteine crystals (mean particle size of 427 μm) at a spray rate of 6.5 g/min with an atomising pressure of 0.8-1.0 bar. The product temperature was kept at 35-42° C. during the coating process. The relative amount of coating in the coated particles was 30 wt.-%. It was found that these coatings provided effective taste-masking.

| Coat | Triglyceride | Wt. % | Surfactant | Wt. % |
|---|---|---|---|---|
| #1 | Dynasan 116 (tripalmitin) | 90 | Labrafil CS 2125 (linoleoyl macrogol-6 glycerides, linoleoyl polyoxyl-6 glycerides, corn oil PEG-6 esters) | 10 |
| #2 | Dynasan 116 (tripalmitin) | 90 | Imwitor 372 (glyceryl stearyl citrate) | 10 |
| #3 | Dynasan 116 (tripalmitin) | 90 | Imwitor 372 (glyceryl stearyl citrate) Dynacet 211 (acetylated glycerides) | 5 5 |
| #4 | Dynasan 114 (trimyristin) | 95 | Span 20 (sorbitan monolaurate) | 5 |
| #5 | Dynasan 114 (trimyristin) | 95 | Tween 80 (polysorbate 80) | 5 |

The invention claimed is:

1. A pharmaceutical composition comprising a coated particle comprising a core and a coating, wherein the core comprises N-acetylcysteine as the pharmacologically active ingredient, and wherein the coating comprises:
   i. a triglyceride selected from the group consisting of glyceryl tripalmitate and glyceryl tristearate, and
   ii. a non-ionic surfactant selected from the group consisting of polysorbates, mono- and di-glycerides of fatty acids, propylene glycol esters, sucrose fatty acid esters, polyglycerol esters, sorbitan fatty acid esters, polyoxyethylene sorbitan fatty acid esters, polyoxyethylene fatty acid ethers, and poloxamers;
   and wherein the coated particle exhibits rapid release of the active ingredient.

2. The pharmaceutical composition of claim 1, being formulated as granules, such as dispersible granules, effervescent granules, direct-to-mouth granules, or as a tablet, such as a dispersible tablet, an effervescent tablet, or an orally disintegrating tablet.

3. The pharmaceutical composition of claim 1, wherein the surfactant is a polysorbate.

4. The pharmaceutical composition of claim 3, wherein the polysorbate is polysorbate 65.

5. The pharmaceutical composition of claim 3, wherein the coating comprises from 70 to 90 wt.-% triglyceride and from 10 to 30 wt.-% polysorbate.

6. The pharmaceutical composition of claim 3, wherein the coating consists of the triglyceride and the polysorbate.

7. The pharmaceutical composition of claim 1, wherein the weight of the coating is from 20 to 70 wt.-% relative to the total weight of the coated particle.

8. The pharmaceutical composition of claim 1, wherein the core consists of N-acetylcysteine.

9. The pharmaceutical composition of claim 1, wherein an amount of the coated particles which is equivalent to a 600 mg dose of N-acetylcysteine releases at least about 85% of the N-acetylcysteine within 15 minutes when placed in vessels filled 900 mL of 0.1 N HCl and stirred at 100 rpm in a USP paddle apparatus.

10. The pharmaceutical composition of claim 9, wherein an amount of the coated particles which is equivalent to a 600 mg dose of N-acetylcysteine releases at least about 95% of the N-acetylcysteine within 15 minutes when placed in vessels filled 900 mL of 0.1 N HCl and stirred at 100 rpm in a USP paddle apparatus.

11. The pharmaceutical composition of claim 1, wherein no significant difference in the release profile is observed after storing the pharmaceutical composition for 3 months in sachets or glass bottles at 25° C/160% r.h., 30° C/65% r.h. or 40° C/75% r.h.

* * * * *